US006890512B2

(12) United States Patent
Roser et al.

(10) Patent No.: US 6,890,512 B2
(45) Date of Patent: May 10, 2005

(54) METHODS OF PREVENTING AGGREGATION OF VARIOUS SUBSTANCES UPON REHYDRATION OR THAWING AND COMPOSITIONS OBTAINED THEREBY

(75) Inventors: Bruce J. Roser, Balsham (GB); Camilo Colaco, Trumpington (GB); Jaap Kampinga, Groningen (NL); Christopher Smith, Huntingdon (GB)

(73) Assignee: Elan Drug Delivery Limited, Nottingham (GB)

( * ) Notice: Subject to any disclaimer, the term of this patent is extended or adjusted under 35 U.S.C. 154(b) by 217 days.

(21) Appl. No.: 09/836,625

(22) Filed: Apr. 16, 2001

(65) Prior Publication Data

US 2001/0055583 A1 Dec. 27, 2001

Related U.S. Application Data

(63) Continuation of application No. 08/252,967, filed on Jun. 2, 1994, now abandoned.

(51) Int. Cl.$^7$ .............................................. A61K 51/00
(52) U.S. Cl. .................... 424/1.29; 424/1.11; 424/1.33; 424/489; 424/499
(58) Field of Search .............................. 424/1.11, 1.29, 424/1.33, 489, 499; 530/350

(56) References Cited

U.S. PATENT DOCUMENTS

| | | |
|---|---|---|
| 3,557,717 A | 1/1971 | Chivers |
| 3,619,294 A | 11/1971 | Black et al. |
| 3,632,357 A | 1/1972 | Childs |
| 3,655,442 A | 4/1972 | Schwer et al. |
| 4,127,502 A | 11/1978 | Li Mutti et al. |
| 4,158,544 A | 6/1979 | Louderback |
| 4,327,076 A | 4/1982 | Puglia et al. |
| 4,327,077 A | 4/1982 | Puglia et al. |
| 4,457,916 A | 7/1984 | Hayashi et al. |
| 4,588,744 A | 5/1986 | McHugh |
| 4,701,417 A | 10/1987 | Portenhauser et al. |
| 4,762,857 A | 8/1988 | Bollin, Jr. et al. |
| 4,865,871 A | 9/1989 | Livesey et al. |
| 4,883,762 A | 11/1989 | Hoskins |
| 4,891,319 A * | 1/1990 | Roser .......................... 435/188 |
| 5,098,893 A | 3/1992 | Franks et al. |
| 5,149,653 A | 9/1992 | Roser |
| 5,242,792 A | 9/1993 | Rudolph et al. |
| 5,290,765 A | 3/1994 | Wettlaufer et al. |
| 5,348,852 A | 9/1994 | Bonderman |
| 5,422,384 A | 6/1995 | Samuels et al. |
| 5,512,547 A | 4/1996 | Johnson et al. |
| 5,612,315 A | 3/1997 | Pikal et al. |
| 5,902,565 A * | 5/1999 | Cox et al. .................. 424/1.29 |

FOREIGN PATENT DOCUMENTS

| | | |
|---|---|---|
| EP | 0 415 567 A2 | 3/1991 |
| EP | 0 762 897 | 3/1997 |
| GB | 2 009 198 A | 6/1979 |
| GB | 2 126 588 A | 3/1984 |
| GB | 2 206 273 A | 1/1989 |
| WO | WO 87/00196 A1 | 1/1987 |
| WO | WO 89/06542 A1 | 7/1989 |
| WO | WO 90/04329 A1 | 5/1990 |
| WO | WO 90/13637 A1 | 11/1990 |
| WO | WO 92/02133 A1 | 2/1992 |
| WO | WO 95/05809 A1 | 2/1995 |
| WO | WO 95/33488 A1 | 12/1995 |
| WO | WO 96/40077 A3 | 12/1996 |
| WO | WO 96/40077 A2 | 12/1996 |

OTHER PUBLICATIONS

Arakawa, T. et al. (1993), "Factors Affecting Short–Term and Long–Term Stabilities of Proteins," *Advanced Drug Delivery Reviews* 10:1–28.

Carpenter, J. F. et al. (1990). "Comparison of Solute–Induced Protein Stabilization in Aqueous Solution and in the Frozen and Dried States," *J. Dairy Sci.* 73(12):3627.3636.

Colaco, C.A.L. S. et al. (1994). "Chemistry of Protein Stabilization by Trehalose" Chapter 14 *In Formulation and Delivery of Proteins and Peptides*, Cleland, J. L. et al. eds. American Chemical Society: Washington, DC. pp. 222–240.

Crowe, J.H. et al. (1990). "Are Freezing and Dehydration Similar Stress Vectors? A Comparison of Modes of Interaction of Stabilizing Solutes with Biomolecules," *Cryobiology* 27:219–231.

Darnell, J. et al. eds. (1986). *Molecular Cell Biology* Scientific American Books, Inc. pp. 59.

De Young, L.R. et al. (1993). "Aggregation and Denaturation of Apomyoglobin in Aqueous Urea Solutions," *Biochemistry* 32:3877–3886.

Heiteftiss, R. et al. (1959). "The Stabilization of Extracts of Cabbage Leaf Proteins by Polyhydroxy Compounds for Electrophoretic and Immunological Studies," *Archives of Biochemistry and Biophysics* 85:200–208.

Lee, J.C. et al. (1981). "The Stabilization of Proteins by Sucrose," *The Journal of Biological Chemistry* 256(14):7193–7201.

Manning, M.C. et al. (1989). "Stability of Protein Pharmaceuticals," *Pharmaceutical Research* 6(11):903–917.

Newman, Y.M. et al. (1993). "The Role of Trehalose and Other Carbohydrates in Biopreservation" *Biotechnology and Genetic Engineering Reviews* 11(5):263–294.

Paborji, M. et al. (1994). "Chemical and Physical Stability of Chimeric L6, a Mouse–Human Monoclonal Antibody," *Pharmaceutical Research* 11(5):764–771.

(Continued)

Primary Examiner—Susan Ungar
Assistant Examiner—Minh-Tam Davis
(74) Attorney, Agent, or Firm—Morrison & Foerster LLP

(57) ABSTRACT

The present invention encompasses methods to prevent aggregation of a wide variety of substances during freezing/thawing and/or dehydrating/rehydrating. The substances thus obtained and compositions comprising the substances are also encompassed by the invention.

5 Claims, 3 Drawing Sheets

OTHER PUBLICATIONS

Pikal, M.J. (1991). "Freeze–Drying of Proteins: Part II: Formulation Selection," *Pharmaceutical Technology International* pp. 40–43.

Piestrelski, S.J. et al. (1993). "Dehydration–Induced Conformational Transitions in Proteins and Their Inhibition by Stabilizers," *Biophysical Journal* 65:661–671.

Schwartz, P.L. et al. (1973). "The Aggregation of [$^{125}$ I] Human Growth Hormone in Response to Freezing and Thawing,"*EndocrInology* 92(6):1795–1798.

Anonymous, (1995). "Biochemicals Organic Compounds for Research and Diagnostice Reagents,"*SiGMA Chemical Company Catalogue*, pp. 995.

Blakeley, D. et al. (Oct. 6, 1990). "Dry Instant Blood Typing Plate for Bedside Use," *Lancet* 336:854–855.

Burgess, W.H. et al. (1990). "Possible Dissociation of the Heparin–Binding and Mitogenic Activities of HeparinBinding (Acidic Fibroblast) Growth Factor–1 from its Receptor–Binding Activities by Site–Directed Mutagenesis of a Single Lysine Residue," *J. Cell. Biol.* 11:2129–2138.

Colaco, C. et al. (Sept. 1992). "Extraordinary Stability of Enzymes Dried in Trehalose: Simplified Molecular Biology," *BIO/Technol.* 10:1007–1011.

Colaco, C. et al. (1992). "Trehalose Stabilisation of Biological Molecules," *Biotechnol. Int'l.* pp. 345–350.

Furtado, M.D.F.D. (1991). "Quality Control of Animal Venoms and of Their Correspondent Antivenoms I. Standardization of the Assay Methods to Analyze the Biochemical and Pharmacological Properties of Venoms from Some Snakes Belonging to the Genus Bothrops and Crotalus by Using Samples of Venoms Dried on at Room Temperature or Lyophilized," *Mem. Inst Butantan* 53(2):149–159. (in original version).

Gillies, S.D. and Wesolowski, J.S. (1990). "Antigen Binding and Biological Activities of Engineered Mutant Chimeric Antibodies with Human Tumor Specificities," *Hum. Antibod. Hybridomas* 1(1):47–54.

Hora, M.S. (1992). "Lyophilized Formulations of Recombinant Tumor Necrosis Factor," *Pharmaceutical Res.* 9(1):33–36.

Hottiger, T. et al. (1994). "The Role of Trehalose Synthesis for the Acquisition of Thermotolerance in Yeast II. Physiological Concentrations of Trehalose Increase the Thermaol Stability of Proteins In Vitro," *Eur. J. Biochem.* 219(1–2):187–193.

Ivins, B.E. (Feb. 1992). "Immunization Against Anthrax with *Bacillus anthracis* Protective Antigen Combined with Adjuvants," *Infection & Immunity* 60(2):662–668.

Lazar, E. et al. (Mar. 1988). "Transforming Growth Factor α: Mutation of Aspartic Acid 47 and Leucine 48 Results in Different Biological Activities," *Mol. & Cell. Biol.* 8(3):1247–1252.

Pikal, M.J. et al. (1991). "The Effects of Formulation Variables on the Stability of Freeze–Dried Human Growth Hormone," *Pharm. Res.* 8:427–436.

Roser, B. (Sep. 1991). "Trehalose Drying: A Novel Replacement for Freeze–Drying," *BioPharm.* 4:47–53.

Roser, B. (Jul. 1991). "Trehalose, A New Approach to Premium Dried Foods," *Trends in Food Sci. & Technol.*, pp. 166–169.

Tanford, C. and Reynolds, J.A. (1976). "Characterization of Membrane Proteins in Detergent Solutions," *Biochim. Biophys. Acta* 457:133–170.

Tanford, C. (1980). *The Hydrophobic Effect: Formation of Micelles and Biological Membranes*. 2nd Edition, John Wiley & Sons: New York, NY. (Table of Contents Only).

Tao, M. and Morrison, S.L. (Oct. 15, 1989). "Studies of Aglycosylated Chimeric Mouse–Human IgG: Role of Carbohydrate in the Structure and Effector Functions Mediated by the Human IgG Constant Region," *J. of Immunol.* 143(8):2595–2601.

Wang, Y.J. et al., eds. (1993). *Stability and Characterization of Protein and Peptide Drugs*. Plenum Press: New York, NY., pp. 1058.

Yousri, R.M. (1980). "Protein Aggregation in Aqueous Casein Solution; Effect of Irradiation, Dose level, Concentration, Storage, and Additives (Carbohydrate and Lipid," *Z. Ernahrungswiss* 19(2):111–121.

* cited by examiner

METHODS OF PREVENTING AGGREGATION OF VARIOUS SUBSTANCES UPON REHYDRATION OR THAWING AND COMPOSITIONS OBTAINED THEREBY

This application is a continuation of U.S. patent application Ser. No. 08/252,967, filed Jun. 2, 1994, now abandoned, the disclosure of which is incorporated herein by reference in its entirety.

FIELD OF THE INVENTION

The present invention relates to methods of preventing the formation of aggregates of various substances upon dehydration and rehydration and upon freezing and thawing. Compositions obtained thereby are also encompassed by the invention.

BACKGROUND OF THE INVENTION

Storage and processing of a wide range of substances in a dehydrated or frozen form is necessary to retain activity, prevent degradation products from forming and to facilitate handling and transport. Unfortunately, upon rehydration or thawing, many substances tend to aggregate, thereby decreasing their effective concentration and often rendering them useless or forming harmful byproducts.

Various methods have been tried to prevent or eliminate such aggregation. For instance, detergents and chaotropic agents are often used to prevent aggregation of proteins in solution. These agents are thought to prevent aggregation mediated by hydrophobic interactions and thus are limited to prevention of aggregation due to this cause. See, e.g., Tanford and Reynolds (1976) Biochim. Biophys. Acta. 457:133; and Tanford, "The Hydrophobic Effect", 2nd Ed., Wiley, N.Y. (1980). Such agents may also not be suitable for use where the substances are to be formulated into therapeutic compositions as they may cause adverse reactions. Aluminum salts in solution are in the form of a highly hydrated colloidal gel and carry a surface charge at any pH outside their isoelectric point. Since each colloidal particle carries the same charge, they mutually repel each other and thus naturally form a stable colloidal gel. When the hydration shell is removed (e.g., by freezing or drying) the particles can contact each other and the surface energy causes aggregation.

Trehalose, α-D-glucopyranosyl-α-D-glucopyranoside, is a naturally occurring, non-reducing disaccharide which was initially found to be responsible for protection of intact plant cells from desiccation. Trehalose has been shown to be useful in preventing denaturation of proteins viruses and foodstuffs during desiccation. U.S. Pat. Nos. 4,891,319; 5,149,653; 5,026,566; Blakeley et al. (1990) Lancet 336: 854–855; Roser (1991) Trends in Food Sci. and Tech. pp.166–169; Colaco et al. (1992) Biotechnol. Internat., pp. 345–350; Roser (1991) BioPharm. 4:47–53; and Colaco et al. (1992) Bio/Tech. 10: 1007–1011.

In the field of protein purification it would be particularly useful to eliminate or prevent the tendency of proteins to aggregate upon rehydration and thawing. This is especially important in the area of biopharmaceuticals where the proteins are often used as an ongoing basis of treatment. In the case where protein aggregates form and are injected into a patient, antibodies may form to the protein which diminish the effectiveness of the treatment.

Thus, it would be useful to prevent aggregation of a wide variety of substances particularly those useful in medicine.

SUMMARY OF THE INVENTION

The invention encompasses a method of reducing aggregation during dehydration and rehydration of substances comprising the steps of adding to a solution or suspension of the substances an amount of trehalose sufficient to prevent aggregation upon rehydration; and dehydrating the solution or suspension. The invention also encompasses the compositions obtained thereby.

The invention further encompasses rehydrating the solution or suspension to obtain a composition substantially lacking aggregates of the substance. The compositions obtained thereby are also encompassed by the invention.

The invention further encompasses a method of reducing aggregation of substances in solution or suspension during freezing comprising the steps of adding to the solution or suspension of the substance an amount of trehalose sufficient to prevent aggregation during freezing; and freezing the solution or suspension. The invention also comprises the compositions obtained thereby.

The invention further comprises the step of thawing the frozen solution or suspension to obtain a composition substantially lacking aggregates of the substance. The compositions obtained thereby are also encompassed by the invention.

A wide variety of substances are suitable for use in the invention including, but not limited to, therapeutic, prophylactic and diagnostic.

When the substance is red blood cells, the method may further comprise the step of fixing the red blood cells prior to adding trehalose. Fixing of red blood cells can be done by any known method including, but not limited to, formaldehyde and glutaraldehyde.

DETAILED DESCRIPTION OF THE INVENTION

Figure 1:
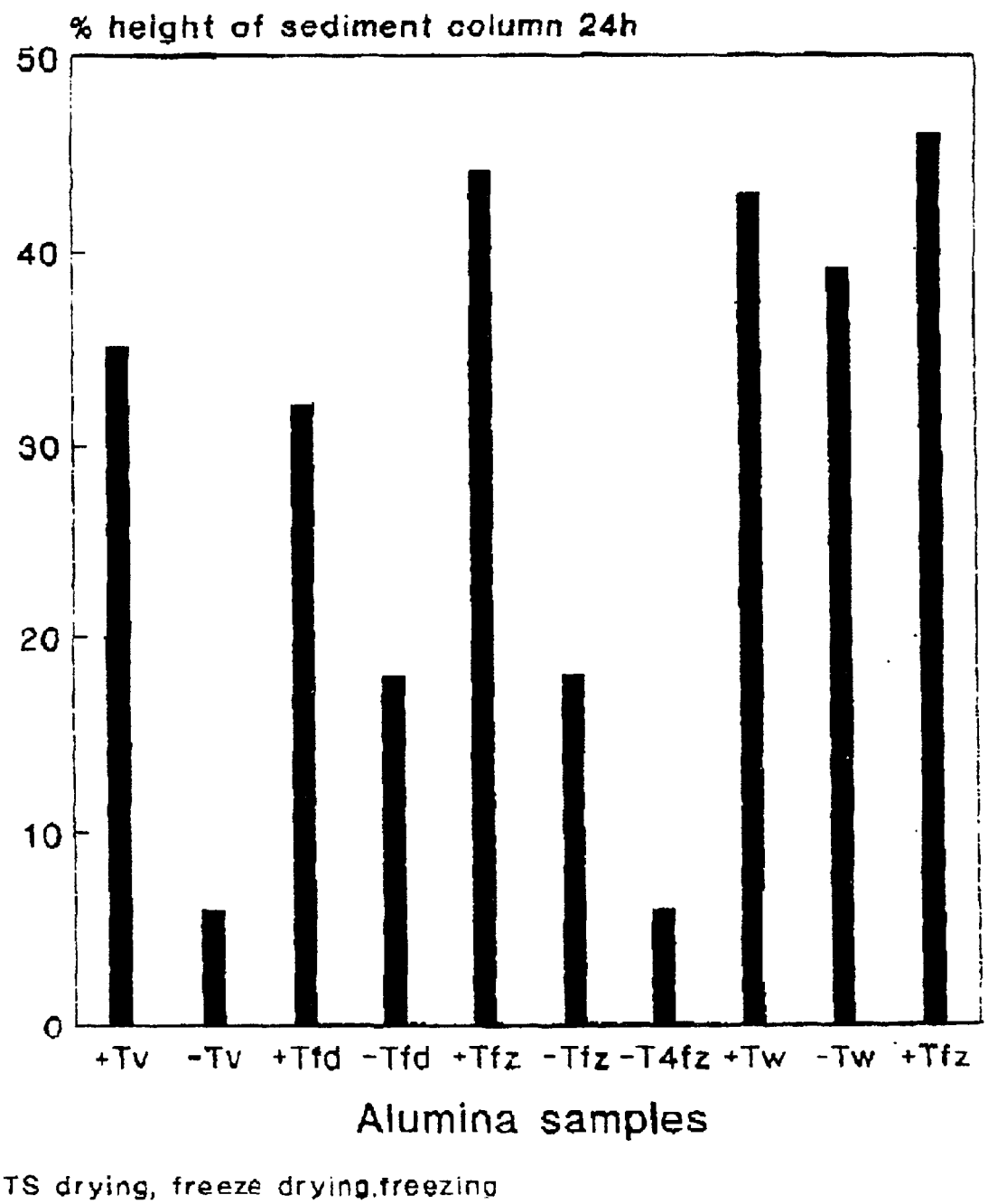
FIG. 1 is a bar graph depicting the percent height of sedimentation of aluminum phosphate per column after 24 hours. Columns labeled with + and − symbols were dried in the presence and absence of trehalose respectively. Tv stands for vacuum drying, Tfd stands for freeze drying, Tfz strands for freezing, T4fz stands for freeze thawing four times and Tw stands for aqueous samples.

The present invention encompasses a method of reducing aggregation during dehydration and rehydration of substances by adding to a solution or suspension of the substances an amount of trehalose sufficient to prevent aggregation upon rehydration; and dehydrating the solution or suspension.

The invention further encompasses a method of reducing aggregation of substances in solution or suspension during freezing and thawing comprising the steps of adding to the solution or suspension of the substance an amount of trehalose sufficient to prevent aggregation during freezing and thawing; and freezing the solution or suspension.

The term "aggregation" as used herein refers to the interaction of two or more molecules of a substance such that they no longer behave as monomers but as dimers, trimers or other multimeric forms. Reducing aggregation decreases the concentration of multimeric forms compared to substances dehydrated and rehydrated or frozen and thawed in the absence of trehalose. A substance substantially free of aggregates or substantially nonaggregated is one which, upon rehydration or thawing, contains a decreased amount of multimeric forms of the substance compared to a control lacking trehalose. Typically, trehalose prevents the formation of all multimeric forms of the substance. In the case of growth hormone, for instance, the addition of trehalose prior to dehydrating or freezing results in the elimination of all multimeric forms with the exception of dimers. The dimers are, however, reduced in comparison to a control.

In a preferred embodiment, the substances suitable for use in the invention have medical utility. Such substances include, but are not limited to, therapeutic substances, prophylactic substances and diagnostic substances. The substances are those which form multimers upon dehydration/rehydration and/or freezing/thawing. The method of formation of multimers or aggregates is not critical to the invention.

Suitable therapeutic substances include, but are not limited to, any therapeutically effective biological modifier. Such modifiers include, but are not limited to, proteins and peptides, steroid hormones, oligosaccharides, nucleic acids and a variety of small molecules. Further, the modifiers may be derived from natural sources made by recombinant or synthetic means and include analogues, agonists and homologs. As used herein "protein" refers also to peptides and polypeptides. Such proteins include, but are not limited to, growth hormones, growth factors, insulin, monoclonal antibodies, interferons and interleukins. Preferably, the growth hormone is human growth hormone. Suitable steroid hormones include, but are not limited to, estrogen, progesterone and testosterone. Therapeutic substances prepared by the methods described herein are also encompassed by the invention.

Suitable prophylactic substances include, but are not limited to, aluminum hydroxide and aluminum phosphate which are used in preparation of vaccines. Compositions containing the prophylactic substances are further encompassed by the invention. Preferable compositions include vaccines containing the aluminum hydroxide or aluminum phosphate prepared by the method described herein. Suitable vaccines include, but are not limited to, combination vaccines, such as diphtheria, tetanus, pertussis (DTP) or DTP/inactivated poliovaccine (IPV). Suitable diagnostic substances include, but are not limited to, colloidal gold, polystyrene latex, fixed erythrocytes and monoclonal antibodies. Diagnostic substances prepared-by the method described herein are also encompassed by the invention.

The dehydration step can be performed by any method known in the art including, but not limited to, lyophilization, drying at ambient conditions or drying under reduced vapor pressure. When drying at reduced vapor pressure, the temperature at which the drying occurs is preferably below the temperature at which degradation of the substance occurs.

The freezing step can be performed by any method known in the art including, but not limited to immersing in liquid nitrogen, placing in a freezer which may be at −4° C. to −80° C., dry ice and alcohol freezing bath. The samples should be maintained at a temperature suitable to maintain the frozen state. Thawing the frozen sample can be by any means known in the art, for instance at room temperature or at an elevated temperature. If thawing occurs at an elevated temperature, the temperature should be below that which causes denaturation or other chemical changes in the substance. Optimal freezing and thawing temperatures can be determined empirically. Such a determination is within the skill of one in the art.

Once the substances have been dehydrated or frozen, they can be stored indefinitely. The dehydrated substances store well at ambient temperatures, although they may be stored at any temperature below that which causes denaturation or other chemical changes. The invention further includes the steps of rehydration of the dehydrated samples to obtain solutions and suspensions substantially free of aggregates of the substance. Rehydration may add at least an amount of water sufficient to restore the buffer composition of the original solution or suspension but may add any amount of water or buffer.

When the substance is red blood cells, the method may further comprise fixing the red blood cells prior to adding trehalose. The fixing step may be done by any method known in the art including, but not limited to, glutaraldehyde. In the preferred embodiment, the cells are fixed.

The methods of the present invention require that the trehalose be present in an amount sufficient to prevent aggregation of the substance upon rehydration or thawing. Such a determination will be made empirically and is well within the skill of one in the art. Preferably, trehalose is added in an amount to obtain a final concentration of from about 1% to 50% (w/v). More preferably, trehalose is added in an amount to obtain a final concentration of from about 5% to 25% (w/v).

Trehalose is available from a variety of suppliers. Preferably the grade of trehalose used is ANALAR reagent, molecular biology or pharmaceutical grade. In the case of medicinal compositions the trehalose preferably meets the good manufacturing practice (GMP) standards set by the Food and Drug Administration (FDA).

The invention also encompasses the products obtained by the method both before and after rehydration or thawing. In one embodiment, the invention includes the frozen compositions containing a substance and an amount of trehalose sufficient to prevent aggregation of the substance upon thawing. In another embodiment, the invention includes a dehydrated composition comprising a substance and an amount of trehalose sufficient to prevent aggregation of the substance upon rehydration. The invention further includes the compositions after being thawed or rehydrated respectively.

Interestingly, the amount of trehalose found to be effective at preventing aggregation cannot be directly extrapolated from the amount of trehalose effective in preventing desiccation damage. For instance, work presented in U.S. Pat. No. 4,891,319 showed that amounts of trehalose as low as 1% w/v in a protein solution could prevent desiccation damage to proteins such as Factor VIII. The Examples presented herein show that more than 30% w/v trehalose is necessary to completely prevent aggregation of aluminum hydroxide and 15% w/v is necessary to prevent aggregation of a protein.

The following examples are meant to illustrate, but not limit, the invention.

EXAMPLES

Example 1

Prevention of Aggregation of Particulate Suspensions by Trehalose

In order to determine whether trehalose prevented aggregation of particulate suspensions, two examples, colloidal gold and polystyrene latex, were studied. Colloidal gold was obtained from the Babraham Laboratories and polystyrene latex was a suspension of particles of polystyrene which had been purchased from Sigma Chemical Company.

The colloidal gold was made according to the method described by Frens (1993) Nature 241:20. It was dried from a concentrated suspension of 0.2% Au in a volume of 50 $\mu$l per well in a 96 well microtiter plate either with added 10% w/v trehalose or without trehalose and subsequently rehydrated after storage for one week at 37° C. in a dry oven. On rehydration, the material that had been dried in the presence of trehalose gave a smooth suspension of colloidal gold as determined by microscopic examination. The material that had been dried without trehalose showed microscopic aggregates which could not be broken up into a smooth suspension.

With the polystyrene latex, similar experiments were done. The latex was obtained from Sigma Chemical Company catalogue number LB-8, average diameter 0.8 micron polystyrene. It was used at the concentration obtained from the supplier and again was dried without any addition and also dried with the addition of 10% w/v trehalose which was dissolved in the solution before drying. Both samples were rehydrated about a week after drying and were stored at 37° C. in a dry oven in the interim. The material dried without trehalose was badly aggregated into very large clumps. The material dried in the presence of trehalose resuspended into a very smooth, single particulate suspension.

Thus, the addition of trehalose prior to drying the particulate suspensions substantially reduced the amount of aggregation upon rehydration compared to a control lacking trehalose.

Example 2

Effect of Trehalose-Drying on Aggregation of Red Blood Cells

Experiment

Rat RBCs were washed three times in an anti-coagulant CPD (102 mM trisodium citrate, 1.08 mM sodium phosphate and 11 mM dextrose), filtered through cotton wool and fixed in either 1% formaldehyde or 0.5% glutaraldehyde. Fixing was at room temperature for one hour. The fixed cells were washed three times in CPD and resuspended in either 10% Trehalose and 0.12 mM Sodium Azide ($NaN_3$) or CPD. The final cell concentration was 25% w/v.

Cells fixed in formaldehyde lysed on washing and were not processed further.

Unfixed cells agglutinated in trehalose and needed the addition of ⅕th volume of Phosphate-buffered saline before being processed further.

100 $\mu$l of cells in either 10% trehalose 0.12 mM $NaN_3$ or CPD were dried either in Nunc plates or on slides and examined microscopically for aggregates.

Results

The unfixed cells dried without trehalose lysed completely and with those dried with trehalose also showed 95–99% lysis though the ghosts showed discoid morphology.

The fixed cells dried without trehalose showed gross macroscopic aggregation of the cells. The fixed cells dried with trehalose resuspended as a smooth single cell suspension with only a few microaggregates. These microaggregates appear to form at higher concentrations of trehalose and thus do not appear to be concentration dependent.

Example 3

Aggregation of Aluminum Hydroxide/Phosphate Sedimentation Assay

The following method was followed to determine whether trehalose is successful in preventing aggregation of prophylactic adjuvants.

Aluminum phosphate and aluminum hydroxide were diluted 5-fold to a final concentration of 0.6% w/v and allowed to sediment in 1 ml glass pipettes. The height of the sediment column was measured at various time intervals up to 24 hours. Note that the % height of sediment column should not be <30% when a steady state has been reached. (about 5 hours.)

The samples were dried under vacuum, frozen at −20° C. and thawed at room temperature.

Results

Pilot 1. Aluminum Phosphate

Different forms of drying and storage were compared in the presence or absence of 15% trehalose. These were vacuum drying (Tv), freeze drying (Tfd), freezing (Tfz) and freeze thawing for four cycles (T4fz). Wet controls (Tw) which were stored at 4° C. were also run.

Figure 2:
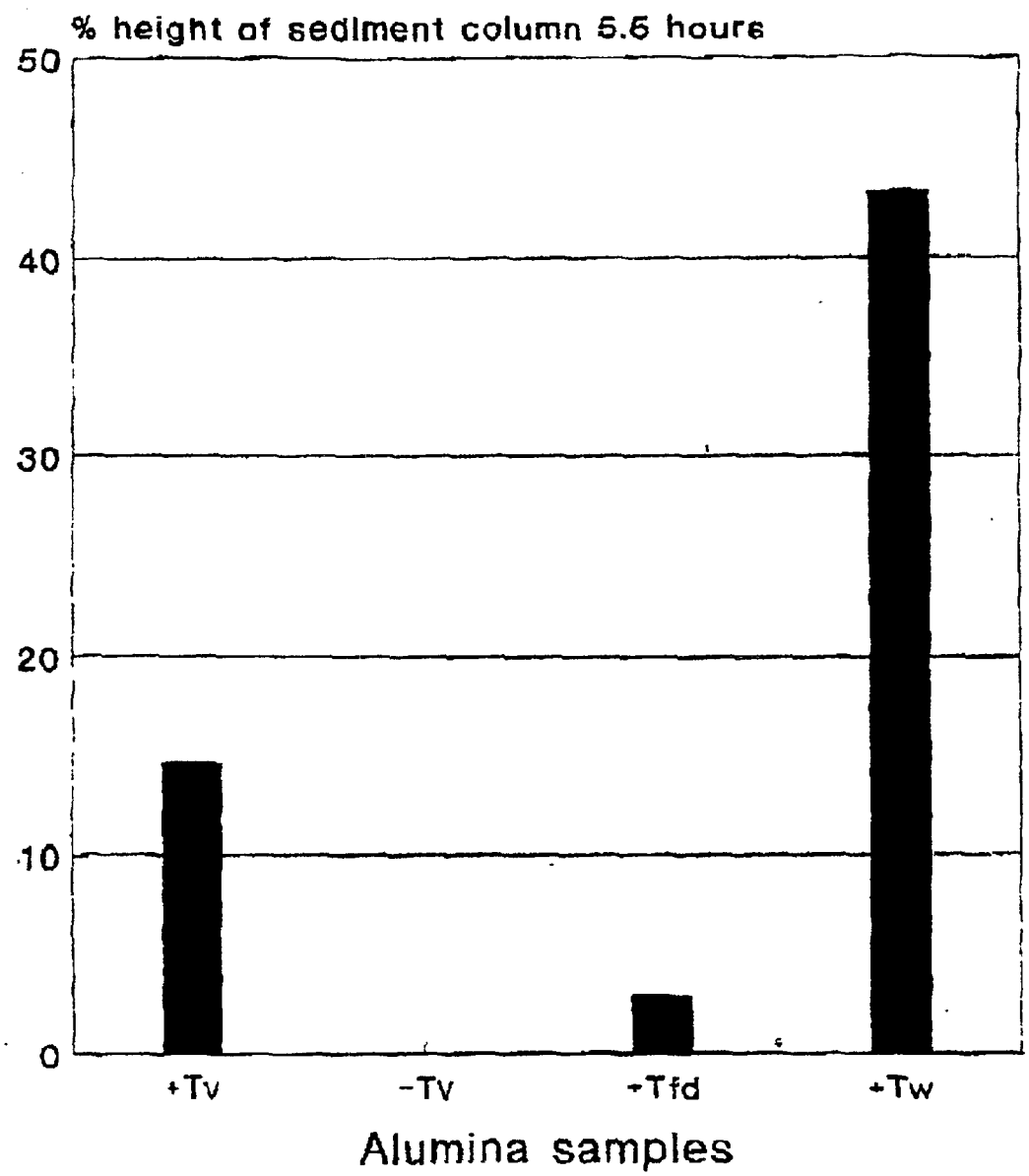
FIG. 2 is a bar graph depicting the percent height of sedimentation of aluminum phosphate per column after 5.5 hours. Prior to testing, samples were stored for one week at 45° C. The abbreviations are the same as those in FIG. 1.

200 $\mu$l sample per glass vial were dried and sedimentation assays carried out at day 0 and after 1 week storage at 45° C. The results obtained are shown in FIGS. 1 and 2.

Figure 3:
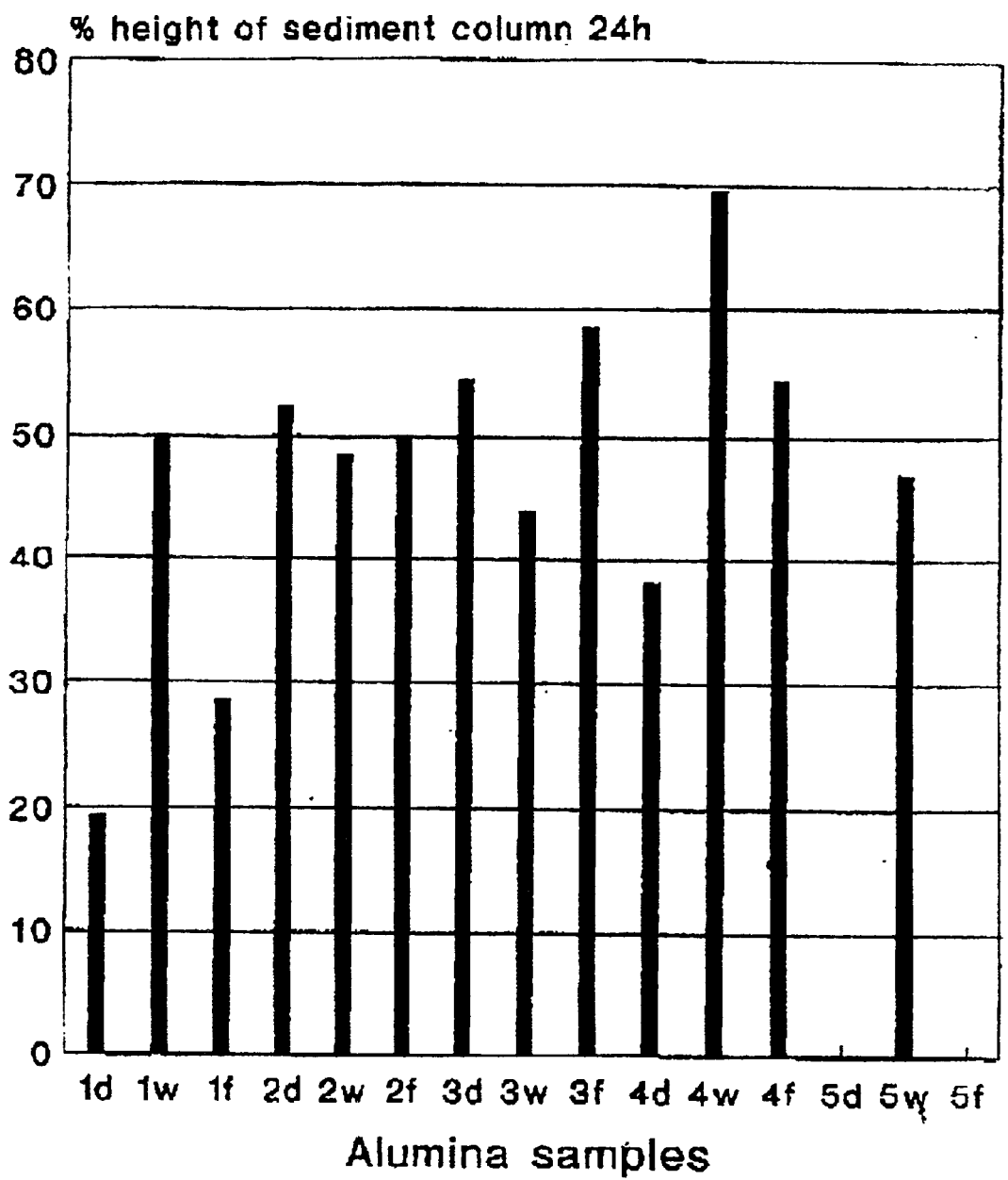
FIG. 3 is a bar graph depicting the percent height of sedimentation of aluminum hydroxide after 24 hours. The numbers refer to the series as described in Example 3, d stands for vacuum drying, w stands for aqueous control, and f stands for freezing.

Pilot 2. The aggregation of aluminum hydroxide and haemaccel (degraded gelatin) was measured with a titration of trehalose with the concentrations shown in Table 1. The samples contained 1.5% aluminum hydroxide and 2% haemaccel. Only vacuum drying (d) and freezing (f) were compared. Wet controls (w) contained trehalose and haemaccel but were not dried or frozen. Each series contained (d), (f) and (w) samples. The concentrations used are shown in Table 1 and the results obtained are shown in FIG. 3.

TABLE 1

| Series | Final % trehalose | % haemaccel |
| --- | --- | --- |
| 1 | 7.5 | — |
| 2 | 15 | — |
| 3 | 30 | — |
| 4 | 15 | 2 |
| 5 | — | — |

Conclusions a) 15% trehalose can prevent freezing induced aggregation in aluminum phosphate and aluminum hydroxide b) 7.5% trehalose is not sufficient for preventing aggregation during the drying process.

c) No additional effect of Haemaccel at 2% was observed.

Aluminum hydroxide, dried in the absence of trehalose and rehydrated was found to be aggregated into large clumps which sedimented rapidly and quickly to yield a very small gel column. Trehalose in concentrations above 15% prevented this aggregation so that the rehydrated material formed a gel column of a height similar to the fresh, undehydrated material. This sedimentation pattern illustrates that the hydrated, nonaggregated molecules have a large hydration shell volume and are separated from one another causing them to sediment slowly.

Example 4

Effect of Trehalose on Aggregation of Biological Molecules

Protein formulations may undergo modification by a number of mechanisms including deamidation, oxidation and aggregation, the principle causes of human growth hormone (hGH) degradation. Deamidation and oxidation are considered collectively as chemical degradation. To date there is little evidence of any effect of these chemical degradation products on biopotency. Pearlman and Bewly (1993) In: Wang and Pearlman eds. *Stability and Characterization of Protein and Peptide Drugs*, pp. 1–58, Plenum Press, New York.

Aggregation is the principle problem affecting hGH and other protein formulations used as biopharmaceuticals and may reduce biopotency. Soluble or insoluble aggregates can form as a result of both covalent and non-covalent interactions. A variety of stresses such as heating, freezing or agitation may induce aggregation. Whilst a visible insoluble aggregate may render a parenteral product unuseable, the major problem is the induction of an unwelcome immune response in the subject. Pearlman and Bewley 1993. This is particularly detrimental where the protein formulations such as hGH are administered parenterally and in multiple doses.

The following experiment was performed to determine whether or not trehalose affected the aggregation of proteins. Samples of hGH (5 mg) were dried from 200 µl containing 15% trehalose, 5 mM $Na_2HPO_4$—$2H_2O$ adjusted to pH 7.4 with $H_3PO_4$ (formulation A). Two control samples were prepared: 5 mg hGH dried from 200 µl sodium phosphate buffer pH 7.4 (formulation B); and 5 mg hGH dried from 200 µl sodium phosphate buffer pH 7.4, 5 mg glycine, 25 mg mannitol (formulation C). These formulations were dried for 20 hours in a vacuum drier at a pressure of 30 millitorr and a shelf temperature of 40° C. They were subsequently sealed under vacuum in standard pharmaceutical serum vials with rubber closures and a crimped aluminum seal.

Following storage at 40° C. in a dry incubator, samples were rehydrated with deionised water and analysed by reverse phase and size exclusion high performance liquid chromatography to determine chemical degradation and aggregation respectively according to the method described by Pikal et al. (1991) Pharm. Res. 8:427–436. These results are presented in Table 2.

Formulation A was subsequently re-analysed and compared with a conventionally freeze-dried essentially as described in Pikal et al. (1991) equivalent formulation (formulation D). These results are presented in Table 3.

Results

An accelerated aging protocol of four weeks at 40° C. was utilized to assess stability and aggregation. The formulation containing trehalose performs very well under these conditions. No chemical degradation was observed and the limited aggregation detected was restricted to dimer formulation (Table 2, lines 1–4). The absence of high molecular weight aggregates is significant.

Two hGH controls were formulated, one without a stabilizing excipient (B) and one containing glycine and mannitol that was similar to commercial formulations (C) (Table 2, lines 5–6). These formulations suffered from considerable chemical degradation and aggregate formation, both dimer and higher molecular weight. The values for the glycine mannitol formulation were comparable with results from a previous study in which a similar formulation was freeze-dried (Table 3, line 7, Pikal, et al. 1991). When the stability of formulation A was compared with that of a freeze-dried equivalent (formulation D), no difference in terms of 40° C. stability was observed (Table 3, lines 1–6). In Tables 2 and 3 chemical degradation is measured by the area under the curve represented by the deamidated protein.

Thus the hGH formulations containing trehalose, either dried at 40° C. or freeze-dried, have been shown to be considerable improvements on previous formulations.

TABLE 2

Summary of hGH Stabilization and Aggregation Data (Part 1)

| Line | Formulation | Treatment | % Chemical Degradation | % Aggregation Dimer | % Aggregation High Mol. Weight |
|---|---|---|---|---|---|
| 1 | A | pre-dry | 3.1 | 0.4 | 0.003 |
| 2 | A | post-dry | 3.3 | 0.6 | 0.06 |
| 3 | A | 2 wk., 40° C. | 3.5 | 0.9 | 0.02 |
| 4 | A | 4 wk., 40° C. | 3.4 | 1.1 | 0.002 |
| 5 | B | 4 wk., 40° C. | 11.1 | 6.9 | 2.1 |
| 6 | C | 4 wk., 40° C. | 8.2 | 2.2 | 0.8 |

TABLE 3

Summary of hGH Stabilization and Aggregation Data (Part 2)

| Line | Formulation | Treatment | % Chemical Degradation | % Aggregation |
|---|---|---|---|---|
| 1 | A | initial | 4.15 | 0.66 |
| 2 | A | 2 wk., 40° C. | 4.16 | 0.92 |
| 3 | A | 4 wk., 40° C. | 4.25 | 1.04 |
| 4 | D | initial | 4.05 | 0.71 |
| 5 | D | 2 wk., 40° C. | 4.09 | 0.86 |
| 6 | D | 4 wk., 40° C. | 4.17 | 0.92 |
| 7 | E | 4 wk., 40° C. | 8.2 | 3.0 |

Although the foregoing invention has been described in some detail by way of illustration and example for purposes of clarity and understanding it will be apparent to those skilled in the art that certain changes and modifications may be practiced. Therefore, the description and examples should not be construed as limiting the scope of the invention, which is delineated by the appended claims.

We claim:

1. A method of preventing aggregation during dehydration and rehydration of particulates in suspension comprising the steps of:
    adding to a particulate suspension a final concentration between 10% and 50% (w/v) of trehalose sufficient to prevent aggregation upon rehydration; and
    dehydrating the suspension.

2. The method according to claim 1, wherein the particulates are selected from the group consisting at colloidal gold and polystyrene latex.

3. The method according to claim 1, wherein the amount of trehalose is at least 30% (w/v).

4. The method according to claim 1, wherein the particulate is aluminum hydroxide and the amount of trehalose is at least 15% (w/v).

5. The method according to claim 4, wherein the amount of trehalose is at least 30% (w/v).

* * * * *